United States Patent [19]

Yonan

[11] B 4,001,244

[45] Jan. 4, 1977

[54] 1-ARYL-3,4-DIHYDRO-2(1H)-ISOQUINOLINE CARBONYL CHLORIDES

[75] Inventor: Peter K. Yonan, Morton Grove, Ill.

[73] Assignee: G. D. Searle & Co., Chicago, Ill.

[22] Filed: Apr. 25, 1975

[21] Appl. No.: 571,638

[44] Published under the second Trial Voluntary Protest Program on March 9, 1976 as document No. B 571,638.

Related U.S. Application Data

[63] Continuation-in-part of Ser. No. 381,505, July 23, 1973, Pat. No. 3,905,982.

[30] Foreign Application Priority Data

July 18, 1974 Greece .................................. 4872

[52] U.S. Cl. .......................................... 260/287 D
[51] Int. Cl.² ..................................... C07D 217/06
[58] Field of Search ........................... 260/287 D

[56] References Cited

UNITED STATES PATENTS

| | | |
|---|---|---|
| 3,483,206 | 12/1969 | Werner .............................. 260/287 |
| 3,524,858 | 8/1970 | Kaminsky et al. ................. 260/287 |
| 3,634,429 | 1/1972 | Leimgruber et al. ............. 260/287 |
| 3,666,763 | 5/1972 | Grethe .............................. 260/289 |

*Primary Examiner*—R. Gallagher
*Assistant Examiner*—David E. Wheeler
*Attorney, Agent, or Firm*—Dragan J. Karadzic; John J. Kolano

[57] ABSTRACT

1-Aryl-3,4-dihydro-2(1H)-isoquinolinecarbonyl chlorides, useful in the preparation of the corresponding carboxamides, are described herein. The subject compounds can be prepared by reacting an 1-aryl-3,4-dihydro-2(1H)-isoquinoline with phosgene.

10 Claims, No Drawings

1-ARYL-3,4-DIHYDRO-2(1H)-ISOQUINOLINE CARBONYL CHLORIDES

The present application is a continuation-in-part of copending application Ser. No. 381,505, filed July 23, 1973, and now U.S. Pat. No. 3,905,982, issued Sept. 16, 1975.

The present invention relates to a group of 3,4-dihydro-2-(1H)-isoquinolinecarbonyl chlorides. More particularly, the present invention relates to a group of compounds of the general formula

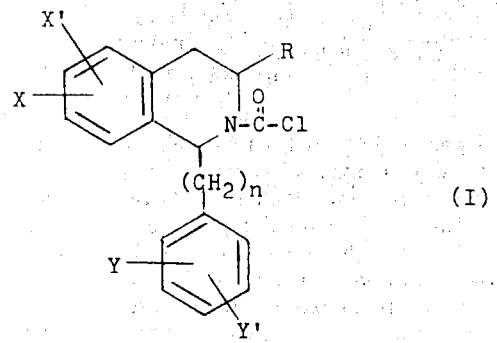

wherein X and X' are each selected from the group consisting of hydrogen, lower alkoxy, benzyloxy, and lower alkyl, or X and X' together represent a single methylenedioxy or ethylenedioxy group; Y and Y' are each selected from the group consisting of hydrogen, halogen, lower alkoxy, and lower alkyl; n is selected from the group consisting of 0 and 1; and R is selected from the group consisting of hydrogen and methyl.

The lower alkoxy groups referred to above contain 1 to 6 carbon atoms and are exemplified by groups such as methoxy, ethoxy, propoxy and isopropoxy. The lower alkyl groups likewise contain 1 to 6 carbon atoms and are exemplified by methyl, ethyl, propyl, isopropyl, and the like. The halogen atoms include fluorine, chlorine, bromine, and iodine.

The compounds of formula (I) can be readily prepared by contacting a compound of the formula

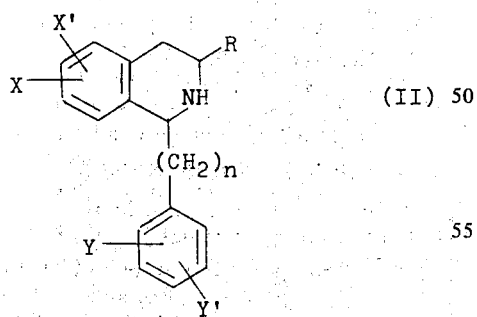

wherein X, X', Y, Y', n, and R are defined as hereinbefore with phosgene.

This reaction is conveniently conducted in a solvent. An especially preferred solvent is benzene, while other possible solvents include aromatic hydrocarbons such as toluene and xylene, halogenated hydrocarbons such as methylene chloride, chloroform and carbon tetrachloride, ketones such as acetone and 2-butanone, and ethers such as ethyl ether, tetrahydrofuran and dioxane. Time and temperature are not critical for the conduct of this reaction, typical temperatures varying from room temperature to reflux and typical times being in the range of a few hours to several days.

The compounds of the present invention are useful as intermediates in the synthesis of the corresponding N-dialkylaminoalkyl and related carboxamides which are useful as antiarrhythmic agents. The conversion of these carbonyl chlorides to the carboxamides and the usefulness of such amides are described in detail in copending application Ser. No. 381,505, filed July 23, 1973.

The invention will appear more fully from the examples which follow. These examples are given by way of illustration only and are not to be construed as limiting the invention either in spirit or in scope as many modifications both in materials and methods will be apparent to those skilled in the art. In these examples, temperatures are given in degrees Centigrade (°C.) and quantities of materials are expressed in parts by weight unless otherwise specified. The relationship between parts by weight and parts by volume is the same as that existing between grams and milliliters. Infrared absorption maxima are given in reciprocal centimeters ($cm^{-1}$).

EXAMPLE 1

A mixture of 50 parts of 3-benzyloxy-4-methoxybenzaldehyde, 25 parts of nitromethane, 2.1 parts of glacial acetic acid and 2.2 parts of n-butylamine in 39.5 parts of ethanol is heated until dissolved. The resulting solution is allowed to stand overnight. The crystals which form are separated by filtration and washed with ethanol. There is thus obtained 3-benzyloxy-4-methoxy-β-nitrostyrene, melting at about 126°–128°C.

Substitution of a like quantity of 4-benzyloxy-3-methoxybenzaldehyde for the 3-benzyloxy-4-methoxybenzaldehyde used above and substantial repetition of the foregoing procedure affords 4-benzyloxy-3-methoxy-β-nitrostyrene, melting at about 118°–121°C.

Substitution of an equivalent quantity of 3,4-methylenedioxybenzaldehyde or 3,4-ethylenedioxybenzaldehyde for the 3-benzyloxy-4-methoxybenzaldehyde used above and substantial repetition of the procedure detailed in the first paragraph of this example affords 3,4-methylenedioxy-β-nitrostyrene, melting at about 159°–162°C., or 3,4-ethylenedioxy-β-nitrostyrene, melting at about 146°–148°C., respectively.

EXAMPLE 2

To a suspension of 20 parts of lithium aluminum hydride in 444 parts of tetrahydrofuran and 177 parts of ethyl ether is added portionwise, over a 1 hour period, a warm solution of 56 parts of 3-benzyloxy-4-methoxy-β-nitrostyrene in 267 parts of tetrahydrofuran. The reaction mixture is refluxed for an additional 2 hours, then is cooled in ice and decomposed by adding 40 parts of water in 71 parts of tetrahydrofuran, followed by 40 parts by volume of a 25% by weight aqueous sodium hydroxide solution, followed by 40 parts of water. The salts are removed by filtration and the filtrate is dried over anhydrous calcium sulfate and stripped of solvent under reduced pressure to afford, as an oil, 3-benzyloxy-4-methoxyphenethylamine.

Substitution of a like quantity of 4-benzyloxy-3-methoxy-β-nitrostyrene for the 3-benzyloxy-4-methoxy-β-nitrostyrene used above and substantial repetition of the foregoing procedure affords, as an oil, 4-benzyloxy-3-methoxy phenethylamine.

Substitution of an equivalent quantity of 3,4-methylenedioxy-β-nitrostyrene or 3,4-ethylenedioxy-β-nitrostyrene for the substituted β-nitrostyrene called for in the first paragraph of this example and substantial repetition of the procedure there detailed affords 3,4-methylenedioxyphenethylamine, as an oil, or 3,4-ethylenedioxyphenethylamine, as an oil, respectively.

EXAMPLE 3

A solution of 45 parts of benzoyl chloride in 149 parts of chloroform is added portionwise over a 30 minute period to a solution of 78 parts of 3-benzyloxy-4-methoxyphenethylamine in 72 parts of triethylamine and 596 parts of chloroform. The mixture is stirred at room temperature for an additional 90 minutes. It is then washed twice with water and once with dilute aqueous sodium bicarbonate solution, dried over anhydrous calcium sulfate and stripped to a low volume under reduced pressure. Addition of n-hexane results in crystallization of N-(3-benzyloxy-4-methoxyphenethyl)benzamide. That product melts at about 136°–138°C.

The above procedure is repeated using a like quantity of 4-benzyloxy-3-methoxyphenethylamine in place of the 3-benzyloxy-4-methoxyphenethylamine. There is thus obtained N-(4-benzyloxy-3-methoxyphenethyl)benzamide, melting at about 128°–130°C.

Substitution of an equivalent quantity of 3,4-methylenedioxyphenethylamine or 3,4-ethylenedioxyphenethylamine for the substituted phenethylamine called for in the first paragraph of this example and substantial repetition of the procedure there detailed affords N-(3,4-methylenedioxyphenethyl)benzamide, melting at about 98°–100°C., or N-(3,4-ethylenedioxyphenethyl)benzamide, melting at 115°–117°C., respectively.

Substitution of an equivalent quantity of 3,4-methylenedioxy-α-methylphenethylamine for the substituted phenethylamine called for in the first paragraph of this example and substantial repetition of the procedure there detailed affords N-(3,4-ethylenedioxy-α-methylphenethyl)benzamide.

EXAMPLE 4

A solution of 64 parts of N-(3-benzyloxy-4-methoxyphenethyl)benzamide and 192 parts of phosphorus oxychloride in 348 parts of toluene is refluxed for 3.5 hours. The solution is stripped in vacuo until a precipitate forms. Ethyl ether is added and the mixture filtered. The solid residue, which is 6-benzyloxy-7-methoxy-1-phenyl-3,4-dihydroisoquinoline hydrochloride, is dissolved in water. Dilute aqueous sodium hydroxide solution is added and the mixture extracted with methylene chloride. The methylene chloride extract is dried over anhydrous calcium sulfate and concentrated to a low volume and n-hexane is then added. The crystals which form are separated by filtration. There is thus obtained 6-benzyloxy-7-methoxy-1-phenyl-3,4-dihydroisoquinoline, melting at about 144°–145°C.

The above procedure is repeated using a like quantity of N-(4-benzyloxy-3-methoxyphenethyl)benzamide in place of the N-(3-benzyloxy-4-methoxyphenethyl)benzamide. In this manner, there is obtained 7-benzyloxy-6-methoxy-1-phenyl-3,4-dihydroisoquinoline, melting at about 134°–137°C.

Substitution of an equivalent quantity of N-(3,4-methylenedioxyphenethyl)benzamide or N-(3,4-ethylenedioxyphenethyl)benzamide for the substituted benzamide called for in the first paragraph of this example and substantial repetition of the procedure there detailed affords 6,7-methylenedioxy-1-phenyl-3,4-dihydroisoquinoline or 6,7-ethylenedioxy-1-phenyl-3,4-dihydroisoquinoline, respectively.

Substitution of an equivalent quantity of N-(3,4-methylenedioxy-α-methylphenethyl)benzamide for the substituted benzamide called for in the first paragraph of this example and substantial repetition of the procedure there detailed affords 6,7-methylenedioxy-3-methyl-1-phenyl-3,4-dihydroisoquinoline.

EXAMPLE 5

A suspension of 38 parts of 6-benzyloxy-7-methoxy-1-phenyl-3,4-dihydroisoquinoline in 435 parts of ethanol is heated to approximately 55°C. 32 Parts of sodium borohydride is added portionwise over a 45 minute period, while maintaining the reaction temperature at 50°–60°C. The mixture is stirred for an additional 3 hours at approximately 50°C. and a precipitate forms. The reaction mixture is then poured into water and the precipitate is separated by filtration, giving 6-benzyloxy-7-methoxy-1-phenyl-1,2,3,4-tetrahydroisoquinoline, melting at about 118°–119°C.

Substitution of a like quantity of 7-benzyloxy-6-methoxy-1-phenyl-3,4-dihydroisoquinoline for the 6-benzyloxy-7-methoxy-1-phenyl-3,4-dihydroisoquinoline used above and substantial repetition of the foregoing procedure affords 7-benzyloxy-6-methoxy-1-phenyl-1,2,3,4-tetrahydroisoquinoline, melting at about 123°–125°C.

Substitution of an equivalent quantity of 6,7-methylenedioxy-1-phenyl-3,4-dihydroisoquinoline or 6,7-ethylenedioxy-1-phenyl-3,4-dihydroisoquinoline for the substituted 3,4-dihydroisoquinoline called for in the first paragraph of this example and substantial repetition of the procedure there detailed affords 6,7-methylenedioxy-1-phenyl-1,2,3,4-tetrahydroisoquinoline, melting at about 94°–96°C., or 6,7-ethylenedioxy-1-phenyl-1,2,3,4-tetrahydroisoquinoline, melting at about 89°–91°C., respectively.

Substitution of an equivalent quantity of 6,7-methylenedioxy-3-methyl-1-phenyl-3,4-dihydroisoquinoline for the substituted 3,4-dihydroisoquinoline called for in the first paragraph of this example and substantial repetition of the procedure there detailed affords 6,7-methylenedioxy-3-methyl-1-phenyl-1,2,3,4-tetrahydroisoquinoline melting at about 89°–91°C.

EXAMPLE 6

50 parts of p-fluorobenzaldehyde and 65 parts of 3,4-dimethoxyphenethylamine are combined and heated over a steam bath in a nitrogen atmosphere for 90 minutes. Then 800 parts by volume of 20% by weight hydrochloric acid is added and heating is continued for an additional 3 hours. The reaction mixture is cooled, made alkaline with sodium hydroxide and extracted with methylene chloride. The organic layer is dried over anhydrous calcium sulfate and stripped in vacuo to give 6,7-dimethoxy-1-(4-fluorophenyl)-1,2,3,4-tetrahydroisoquinoline. After crystallization from a mixture of ethyl ether and n-hexane, that product melts at about 145°–150°C.

When the above procedure is repeated using the appropriately substituted benzaldehyde and 3,4-dimethoxyphenethylamine, the following compounds are obtained:

1-(4-chlorophenyl)-6,7-dimethoxy-1,2,3,4-tetrahydroisoquinoline, melting at about 110°–111°C.

6,7-dimethoxy-1-(2-ethoxyphenyl)-1,2,3,4-tetrahydroisoquinoline, as an oil.

1-(2-bromophenyl)-6,7-dimethoxy-1,2,3,4-tetrahydroisoquinoline, as an oil.

1-(2,6-dichlorophenyl)-6,7-dimethoxy-1,2,3,4-tetrahydroisoquinoline, as a low melting solid.

6,7-dimethoxy-1-(2-tolyl)-1,2,3,4-tetrahydroisoquinoline, as an oil.

1-(2-chlorophenyl)-6,7-dimethoxy-1,2,3,4-tetrahydroisoquinoline, as an oil.

EXAMPLE 7

To a mixture of 26 parts of 6,7-dimethoxy-1-phenyl-1,2,3,4-tetrahydroisoquinoline and 11 parts of triethylamine in 220 parts of benzene is added portionwise, at room temperature over a 40 minute period, 160 parts of a benzene solution containing 20 parts of phosgene. After the addition is complete, the reaction mixture is stirred at room temperature for an additional 90 minutes, then is heated up to reflux for 30 minutes and filtered. The filtrate is evaporated to afford a residual solid, ethyl ether is added and the mixture filtered. The solid thus obtained is 6,7-dimethoxy-1-phenyl-3,4-dihydro-2(1H)-isoquinolinecarbonyl chloride, melting at about 151°–152°C.

When the above procedure is repeated using phosgene and the appropriate 1,2,3,4-tetrahydroisoquinoline, the following compounds are obtained:

6,7-Dimethoxy-1-(4-methoxyphenyl)-3,4-dihydro-2(1H)-isoquinolinecarbonyl chloride, melting at 113°–120°C.

6,7-Dimethoxy-1-(3,4-dimethoxyphenyl)-3,4-dihydro-2(1H)-isoquinolinecarbonyl chloride, as an oil.

1-Phenyl-3,4-dihydro-2(1H)-isoquinolinecarbonyl chloride, as an oil.

6-Benzyloxy-7-methoxy-1-phenyl-3,4-dihydro-2(1H)-isoquinolinecarbonyl chloride, as a waxy solid.

7-Benzyloxy-6-methoxy-1-phenyl-3,4-dihydro-2(1H)-isoquinolinecarbonyl chloride, as a waxy solid.

1-Benzyl-6,7-dimethoxy-3,4-dihydro-2(1H)-isoquinolinecarbonyl chloride, melting at about 124°–125°C.

1-(4-Chlorophenyl)-6,7-dimethoxy-3,4-dihydro-2(1H)-isoquinolinecarbonyl chloride, melting at about 42°–60°C.

6,7-Dimethoxy-1-(4-fluorophenyl)-3,4-dihydro-2(1H)-isoquinolinecarbonyl chloride, melting at about 133°–135°C.

7-Methyl-1-phenyl-3,4-dihydro-2(1H)-isoquinolinecarbonyl chloride.

6,7-Methylenedioxy-1-phenyl-3,4-dihydro-2(1H)-isoquinolinecarbonyl chloride, melting at about 102°–104°C.

6,7-Ethylenedioxy-1-phenyl-3,4-dihydro-2-(1H)-isoquinolinecarbonyl chloride, melting at about 111°–113°C.

6,7-Dimethoxy-1-(2-ethoxyphenyl)-3,4-dihydro-2(1H)-isoquinolinecarbonyl chloride, melting at 135°–136°C.

1-(2-Bromophenyl)-6,7-dimethoxy-3,4-dihydro-2(1H)-isoquinolinecarbonyl chloride, melting at about 130°–132°C.

1-(2,6-Dichlorophenyl)-6,7-dimethoxy-3,4-dihydro-2(1H)-isoquinolinecarbonyl chloride, melting at about 158°–159°C.

6,7-Dimethoxy-1-(2-tolyl)-3,4-dihydro-2(1H)-isoquinolinecarbonyl chloride, melting at 168°–170°C.

1-(2-Chlorophenyl)-6,7-dimethoxy-3,4-dihydro-2(1H)-isoquinolinecarbonyl chloride, melting at about 134°–136°C.

6,7-Dimethoxy-3-methyl-1-phenyl-3,4-dihydro-2(1H)-isoquinolinecarbonyl chloride, melting at about 127°–128°C.

EXAMPLE 8

A solution of 2.0 parts of 2-chloroethylisocyanate in approximately 14 parts of methylene chloride is added portionwise, at room temperature, to 5.0 parts of 6,7-dimethoxy-1-phenyl-1,2,3,4-tetrahydroisoquinoline in 27 parts of methylene chloride. The reaction mixture is stirred for 2 hours, then is stripped of solvent under reduced pressure. The residue is triturated with ether giving, as a solid, N-(2-chloroethyl)-6,7-dimethoxy-1-phenyl-3,4-dihydro-2(1H)-isoquinolinecarboxamide.

EXAMPLE 9

To 10 parts by volume of 2-diethylaminoethylamine is added 3.0 parts of 6,7-dimethoxy-1-phenyl-3,4-dihydro-2(1H)-isoquinolinecarbonyl chloride. An exothermic reaction ensues. The mixture is heated over a steam bath for approximately 30 minutes. (Alternatively, the mixture is maintained at room temperature overnight.) The reaction mixture is then poured into water and extracted with ethyl ether. The ether layer is dried over anhydrous calcium sulfate and evaporated to dryness. The solid thus obtained is crystallized from a mixture of ethyl ether and n-hexane to afford N-(2-diethylaminoethyl)-6,7-dimethoxy-1-phenyl-3,4-dihydro-2(1H)-isoquinolinecarboxamide, melting at about 97°–98°C.

Substitution of an equivalent quantity of 2-diisopropylaminoethylamine for the 2-diethylaminoethylamine used above and substantial repetition of the foregoing procedure affords N-(2-diisopropylaminoethyl)-6,7-dimethoxy-1-phenyl-3,4-dihydro-2(1H)-isoquinolinecarboxamide, melting at about 109°–110°C.

EXAMPLE 10

When an equivalent quantity of 2-piperidinoethylamine is substituted for the 2-diethylaminoethylamine used in Example 9 and the procedure described in the first paragraph of that example is substantially repeated, there is obtained, after crystallization from ethyl ether, 6,7-dimethoxy-1-phenyl-N-(2-piperidinoethyl)-3,4-dihydro-2(1H)-isoquinolinecarboxamide. That compound melts at about 101°–102°C.

EXAMPLE 11

An equivalent quantity of 2-morpholinoethylamine is substituted for the 2-diethylaminoethylamine employed in Example 9 and the procedure described in the first paragraph of that example is repeated. After the mixture is heated over a steam bath for 30 minutes, it was poured into water and extracted with methylene chloride. The methylene chloride extract is then stripped of solvent in vacuo and the residue crystallized from a mixture of methylene chloride and ethyl ether. The product obtained in this manner is 6,7-dimethoxy-N-(2-morpholinoethyl)-1-phenyl-3,4-dihydro-2(1H)- isoquinolinecarboxamide, melting at about 130°–131°C.

EXAMPLE 12

3.0 Parts of 6,7-dimethoxy-1-phenyl-3,4-dihydro-2(1H)-isoquinolinecarbonyl chloride and 10 parts by volume of 3-diethylaminopropylamine are cooled and then combined in the cold. The resultant mixture is allowed to stand at room temperature overnight, then is poured into water and extracted with ethyl ether. The ether extract is dried over anhydrous calcium sulfate, concentrated to a small volume under reduced pressure and cooled in ice to effect crystallization. There is thus obtained N-(3-diethylaminopropyl)-6,7-dimethoxy-1-phenyl-3,4-dihydro-2(1H)-isoquinolinecarboxamide melting at about 92°–93°C.

Repetition of the above procedure using an equivalent quantity of 2-dimethylaminoethylamine affords 6,7-dimethoxy-N-(2-dimethylaminoethyl)-1-phenyl-3,4-dihydro-2(1H)-isoquinolinecarboxamide melting at about 60°C.

In a similar manner, substitution of an equivalent quantity of 3-dimethylaminopropylamine in the procedure detailed above affords 6,7-dimethoxy-N-(3-dimethylaminopropyl)-1-phenyl-3,4-dihydro-2(1H)-isoquinolinecarboxamide.

EXAMPLE 13

To a mixture of 2.5 parts of 2-diisopropylaminoethylamine and 12 parts of triethylamine in approximately 225 parts of chloroform is added portionwise, at room temperature, a solution of 5.0 parts of 6,7-dimethoxy-1-(4-methoxyphenyl)-3,4-dihydro-2(1H)-isoquinolinecarbonyl chloride in about 75 parts of chloroform. The reaction mixture is stirred for 3 to 5 hours, allowed to stand overnight and then poured into water. The chloroform layer is separated, dried over anhydrous calcium sulfate and stripped of solvent under reduced pressure. The resultant oil is triturated with n-hexane to give a solid. Crystallization of that solid from ethyl ether affords N-(2-diisopropylaminoethyl)-6,7-dimethoxy-1-(4-methoxyphenyl)-3,4-dihydro-2(1H)-isoquinolinecarboxamide as a low melting solid. That compound is characterized by infrared absorption maxima in chloroform at about 1640 and 3400 $cm^{-1}$.

Substitution of an equivalent quantity of 2-[N-cyclohexyl(methylamino)]ethylamino for the 2-diisopropylaminoethylamine used above and substantial repetition of the foregoing procedure affords N- 2-[N-cyclohexyl(methylamino)]ethyl -6,7-dimethoxy-1-(4-methoxyphenyl)-3,4-dihydro-2(1H)-isoquinolinecarboxamide, as a low melting solid. That compound exhibits infrared absorption maxima in chloroform at about 1640 and 3420 $cm^{-1}$.

Substitution of an equivalent quantity of N,N,N'-trimethylethylenediamine for the 2-diisopropylaminoethylamine used above and substantial repetition of the foregoing procedure affords 6,7-dimethoxy-N-(2-dimethylaminoethyl)-1-(4-methoxyphenyl)-N-methyl-3,4-dihydro-2(1H)-isoquinolinecarboxamide.

In a similar manner, use of equivalent quantities of N,N,N'-triisopropylethylenediamine and 6,7-dimethoxy-1-phenyl-3,4-dihydro-2(1H)-isoquinolinecarbonyl chloride in place of the dialkylaminoalkylamine and isoquinolinecarbonyl chloride employed above affords N-(2-diisopropylaminoethyl)-6,7-dimethoxy-N-isopropyl-1-phenyl-3,4-dihydro-2(1H)-isoquinolinecarboxamide.

EXAMPLE 14

4.0 Parts of 2-diisopropylaminoethylamine in 75 parts of chloroform is added portionwise, at room temperature, to a mixture of 8.0 parts of 6,7-dimethoxy-1-(3,4-dimethoxyphenyl)-3,4-dihydro-2(1H)-isoquinolinecarbonyl chloride and 15 parts of triethylamine in 225 parts of chloroform. After the addition is complete, the mixture is stirred for 3 to 4 hours, allowed to stand overnight, and then washed with water. The chloroform layer is separated, dried over anhydrous calcium sulfate and concentrated under reduced pressure. The solid material obtained in this manner is crystallized from ether to give N-(2-diisopropylaminoethyl)-6,7-dimethoxy-1-(3,4-dimethoxyphenyl)-3,4-dihydro-2(1H)-isoquinolinecarboxamide, melting at about 114°–115°C.

When the appropriately substituted 3,4-dihydro-2(1H)-isoquinolinecarbonyl chloride is reacted with the appropriate diamine according to the above procedure, the following compounds are obtained:

N-{2-[N-Cyclohexyl(methylamino)]ethyl}-6,7-dimethoxy-1-(3,4-dimethoxyphenyl)-3,4-dihydro-2(1H)-isoquinolinecarboxamide, melting at about 112°–113°C. after crystallization from ethyl ether.

N-(2-Diisopropylaminoethyl)-1-phenyl-3,4-dihydro-2(1H)-isoquinolinecarboxamide, melting at about 101°–103°C. after crystallization from a mixture of ethyl ether and n-hexane.

N-{2-[N-Cyclohexyl(methylamino)]ethyl}-6,7-dimethoxy-1-phenyl-3,4-dihydro-2(1H)-isoquinolinecarboxamide, melting at about 136°–138°C. after crystallization from a mixture of methylene chloride and n-hexane.

6-Benzyloxy-N- 2-[N-cyclohexyl(methylamino)]ethyl 7-methoxy-1-phenyl-3,4-dihydro-2(1H)-isoquinolinecarboxamide melting at 109°–110°C. after crystallization from ethyl ether.

6-Benzyloxy-N-(2-diisopropylaminoethyl)-7-methoxy-1-phenyl-3,4-dihydro-2(1H)-isoquinolinecarboxamide, melting at about 150°–152°C. after crystallization from a mixture of methylene chloride and n-hexane.

7-Benzyloxy-N-(2-diisopropylaminoethyl)-6-methoxy-1-phenyl-3,4-dihydro-2(1H)-isoquinolinecarboxamide, melting at about 142°–144°C. after crystallization from a mixture of methylene chloride and n-hexane.

7-Benzyloxy-N-{2-[N-cyclohexyl(methylamino)-]ethyl}-6-methoxy-1-phenyl-3,4-dihydro-2(1H)-isoquinolinecarboxamide, melting at about 109°–111°C after crystallization from a mixture of methylene chloride and n-hexane.

1-Benzyl-N-(2-diisopropylaminoethyl)-6,7-dimethoxy-3,4-dihydro-2(1H)-isoquinolinecarboxamide, melting at about 87°–89°C. after crystallization from n-hexane.

1-(4-Chlorophenyl)-N-{2-[N-cyclohexyl(methylamino)]-ethyl}-6,7-dimethoxy-3,4-dihydro-2(1H)-isoquinolinecarboxamide, melting at about 142°–143°C. after crystallization from a mixture of methylene chloride and n-hexane.

1-(4-Chlorophenyl)-N-(2-diisopropylaminoethyl)-6,7-dimethoxy-3,4-dihydro-2(1H)-isoquinolinecarboxamide, melting at about 128°–129°C. after crystallization from a mixture of ethyl ether and n-hexane.

N-(2-Diisopropylaminoethyl)-6,7-dimethoxy-1-(4-fluorophenyl)-3,4-dihydro-2(1H)-isoquinolinecarboxamide, melting at about 136°–137°C. after crystallization from a mixture of methylene chloride and n-hexane.

N-{2-[N-Cyclohexyl(methylamino)]ethyl}-6,7-dimethoxy-1-(4-fluorophenyl)-3,4-dihydro-2(1H)-isoquinolinecarboxamide, which melts at about 149°–150°C. after crystallization from a mixture of methylene chloride and N-hexane.

6,7-Dimethoxy-1-(4-fluorophenyl)-N-(2-hexamethyleniminoethyl)-3,4-dihydro-2(1H)-isoquinolinecarboxamide, melting at about 95°–96°C. after crystallization from a mixture of ethyl ether and n-hexane.

6,7-Dimethoxy-1-phenyl-N-[2-(4-phenylpiperidino)ethyl]-3,4-dihydro-2(1H)-isoquinolinecarboxamide, melting at about 166°–167°C. after recrystallization from a mixture of methylene chloride and n-hexane.

N-(2-Diisopropylaminoethyl)-6,7-methylenedioxy-1-phenyl-3,4-dihydro-2(1H)-isoquinolinecarboxamide, melting at about 121°–122°C. after recrystallization from a mixture of ethyl ether and n-hexane.

N-(2-Diisopropylaminoethyl)-6,7-ethylenedioxy-1-phenyl-3,4-dihydro-2(1H)-isoquinolinecarboxamide, melting at about 112°–113°C. after recrystallization from a mixture of ethyl ether and n-hexane.

N-(2-Diisopropylaminoethyl)-6,7-dimethoxy-1-(2-ethoxyphenyl)-3,4-dihydro-2(1H)-isoquinolinecarboxamide, melting at about 127°–128°C. after recrystallization from ethyl ether.

1-(2-Bromophenyl)-N-(2-diisopropylaminoethyl)-6,7-dimethoxy-3,4-dihydro-2(1H)-isoquinolinecarboxamide melting at about 143°–145°C. after recrystallization from a mixture of ethanol and ethyl ether.

1-(2,6-Dichlorophenyl)-N-(2-diisopropylaminoethyl)-6,7-dimethoxy-3,4-dihydro-2(1H)-isoquinolinecarboxamide melting at about 106°–107°C. after recrystallization from a mixture of ethyl ether and n-hexane.

N-(2-Diisopropylaminoethyl)-6,7-dimethoxy-1-(2-tolyl)-3,4-dihydro-2(1H)-isoquinolinecarboxamide, melting at about 230°–233°C. after recrystallization from a mixture of ethanol and ethyl ether.

N-{2-[N-Cyclohexyl(methylamino)]ethyl}-6,7-dimethoxy-1-(2-tolyl)-3,4-dihydro-2(1H)-isoquinolinecarboxamide, melting at about 145°–146°C. after recrystallization from a mixture of methylene chloride and n-hexane.

1-(2-Bromophenyl)-N-{2-[N-cyclohexyl(methylamino)]-ethyl}-6,7-dimethoxy-3,4-dihydro-2(1H)-isoquinolinecarboxamide, melting at about 139°–140°C. after recrystallization from a mixture of methylene chloride and n-hexane.

1-(2-Bromophenyl)-6,7-dimethoxy-N-(2-hexamethyleniminoethyl)-3,4-dihydro-2(1H)-isoquinolinecarboxamide, melting at about 146°–149°C. after recrystallization from ethyl ether.

6,7-Dimethoxy-N-(2-hexamethyleniminoethyl)-1-(2-tolyl)-3,4-dihydro-2(1H)-isoquinolinecarboxamide, melting at about 165°–167°C. after recrystallization from ethyl ether.

N-{2-[N-Cyclohexyl(methylamino)]ethyl}-6,7-dimethoxy-1-(2-ethoxyphenyl)-3,4-dihydro-2(1H)-isoquinolinecarboxamide, melting at about 136°–137°C. after recrystallization from a mixture of ethyl ether and n-pentane.

6,7-Dibenzyloxy-N-(2-diisopropylaminoethyl)-1-phenyl-3,4-dihydro-2(1H)-isoquinolinecarboxamide melting at about 132°–133°C. after recrystallization from a mixture of methylene chloride and n-hexane.

N-{2-[N-Cyclohexyl(methylamino)]ethyl}-6,7-dibenzyloxy-1-phenyl-3,4-dihydro-2(1H)-isoquinolinecarboxamide, melting at about 123°–124°C. after recrystallization from a mixture of methylene chloride and n-hexane.

1-Benzyl-N- 2-[N-cyclohexyl(methylamino)]ethyl - 6,7-dimethoxy-3,4-dihydro-2(1H)-isoquinolinecarboxamide, as an oil.

6,7-Dimethoxy-N-[2-(4-methyl-1-piperazinyl)ethyl]-1-phenyl-3,4-dihydro-2(1H)-isoquinolinecarboxamide.

6,7-Dimethoxy-1-phenyl-N-[2-(1-pyrrolidinyl)ethyl]-3,4-dihydro-2(1H)-isoquinolinecarboxamide.

N-{2-[N-Cyclohexyl(methylamino)]ethyl}-6,7-methylenedioxy-1-phenyl-3,4-dihydro-2(1H)-isoquinolinecarboxamide.

N-{2-[N-Cyclohexyl(methylamino)]ethyl}-6,7-ethylenedioxy-1-phenyl-3,4-dihydro-2(1H)-isoquinolinecarboxamide.

N-(2-Diisopropylaminoethyl)-7-methyl-1-phenyl-3,4-dihydro-2(1H)-isoquinolinecarboxamide.

1-(2-Chlorophenyl)-N-(2-diisopropylaminoethyl)-6,7-dimethoxy-3,4-dihydro-2(1H)-isoquinolinecarboxamide melting at about 78°–81°C. after recrystallization from n-hexane.

N-(2-Diisopropylaminoethyl)-6,7-methylenedioxy-3-methyl-1-phenyl-3,4-dihydro-2(1H)-isoquinolinecarboxamide, as an oil.

1-(2-Chlorophenyl)-N-{2-[N-cyclohexyl(methylamino)]ethyl}-6,7-dimethoxy-3,4-dihydro-2(1H)-isoquinolinecarboxamide melting at about 126°–129°C. after recrystallization from a mixture of methylene chloride and n-hexane.

EXAMPLE 15

A mixture of 3.0 parts of the N-(2-chloroethyl)-6,7-dimethoxy-1-phenyl-3,4-dihydro-2(1H)-isoquinolinecarboxamide prepared in Example 8 and 4.3 parts of piperidine in approximately 40 parts of 2-butanone is heated at 65°C. for 20 hours. The reaction mixture is then stripped in vacuo and the residue taken up in dilute aqueous potassium bicarbonate solution and methylene chloride. The organic layer is dried and stripped in vacuo and the residue is crystallized from ether to afford 6,7-dimethoxy-1-phenyl-N-(2-piperidinoethyl)-3,4-dihydro-2(1H)-isoquinolinecarboxamide, melting at about 101°–102°C.

Substitution of an equivalent quantity of 4-benzylpiperidine in place of the piperidine used above and substantial repetition of the foregoing procedure affords N-[2-(4-benzylpiperidino)ethyl]-6,7-dimethoxy-1-phenyl-3,4-dihydro-2(1H)-isoquinolinecarboxamide.

Substitution of an equivalent quantity of 1-phenylpiperazine in place of the piperidine employed in the procedure detailed in the first paragraph of this example affords 6,7-dimethoxy-1-phenyl-N-[2-(4-phenyl-1-piperazinyl)ethyl]-3,4-dihydro-2(1H)-isoquinolinecarboxamide.

Substitution of an equivalent quantity of diisopropylamine in place of the piperidine employed in the procedure detailed in the first paragraph of this example affords N-(2-diisopropylaminoethyl)-6,7-dimethoxy-1-phenyl-3,4-dihydro-2(1H)-isoquinolinecarboxamide, melting at about 109°–110°C.

In a similar manner, use of N-cyclohexylmethylamine in place of the piperidine used above and 6-benzyloxy-N-(2-chloroethyl)-7-methoxy-1-phenyl-3,4-dihydro-2(1H)-isoquinolinecarboxamide in place of the N-(2-chloroethyl)-6,7-dimethoxy-1-phenyl-3,4-dihydro-2(1H)-isoquinolinecarboxamide used above and repetition of the procedure detailed in the first paragraph of this example affords 6-benzyloxy-N-{2-[N-cyclohexyl(methylamino)]ethyl}-7-methoxyl-1-phenyl-3,4-dihydro-2(1H)-isoquinolinecarboxamide melting at 109°–110°C.

EXAMPLE 16

2.0 Parts of 6-benzyloxy-N-(2-diisopropylaminoethyl)-7-methoxy-1-phenyl-3,4-dihydro-2(1H)-isoquinolinecarboxamide is dissolved in approximately 80 parts of methanol. 0.2 Part of a 5% palladium-on-carbon catalyst is added and the mixture is shaken at room temperature and a pressure of about 2 psi for approximately 23 hours or until one molecular equivalent of hydrogen has been absorbed. The catalyst is removed by filtration and the filtrate is concentrated under reduced pressure to give an oil which solidified upon trituration with n-pentane. That solid is crystallized from a mixture of methylene chloride and n-hexane to afford N-(2-diisopropylaminoethyl)-6-hydroxy-7-methoxy-1-phenyl-3,4-dihydro-2(1H)-isoquinolinecarboxamide, melting at about 91°–92°C.

The procedure described above is repeated using 6-benzyloxy-N-{2-[N-cyclohexyl(methylamino)]ethyl}-7-methoxy-1-phenyl-3,4-dihydro-2(1H)-isoquinolinecarboxamide. Obtained in this manner is N-{2-[N-cyclohexyl(methylamino)]ethyl}-6-hydroxy-7-methoxy-1-phenyl-3,4-dihydro-2(1H)-isoquinolinecarboxamide, an amorphous solid which exhibits infrared absorption maxima in chloroform at about 1635, 3420 and 3560 cm$^{-1}$.

Repetition of the procedure detailed in the first paragraph of this example using 7-benzyloxy-N-(2-diisopropylaminoethyl)-6-methoxy-1-phenyl-3,4-dihydro-2(1H)-isoquinolinecarboxamide affords N-(2-diisopropylaminoethyl)-7-hydroxy-6-methoxy-1-phenyl-3,4-dihydro-2(1H)-isoquinolinecarboxamide. That compound is obtained as an amorphous solid and is characterized by infrared absorption maxima in chloroform at about 1635, 3400 and 3560 cm$^{-1}$.

Repetition of the procedure detailed in the first paragraph of this example using 6,7-dibenzyloxy-N-(2-diisopropylaminoethyl)-1-phenyl-3,4-dihydro-2(1H)-isoquinolinecarboxamide affords 6,7-dihydroxy-N-(2-diisopropylaminoethyl)-1-phenyl-3,4-dihydro-2(1H)-isoquinolinecarboxamide, an amorphous solid.

EXAMPLE 17

2.0 Parts of N-(2-diisopropylaminoethyl)-1-phenyl-3,4-dihydro-2(1H)-isoquinolinecarboxamide is dissolved in 22.8 parts of methyl iodide and placed in a steam oven at 65°C. for about 16 hours. The reaction mixture is then concentrated under reduced pressure and the residue is dissolved in ethanol. Ethyl ether is added and the mixture is refrigerated until crystallization occurs. The product, which is N-(2-diisopropylaminoethyl)-1-phenyl-3,4-dihydro-2(1H)-isoquinolinecarboxamide methiodide, is separated and recrystallized from the mixture of ethanol and ethyl ether.

EXAMPLE 18

4.4 Parts of N-(2-diisopropylaminoethyl)-6,7-dimethoxy-1-phenyl-3,4-dihydro-2(1H)-isoquinolinecarboxamide is dissolved in 110 parts of dimethylsulfoxide. Then 0.24 part of sodium hydride, as a 56% suspension in mineral oil, is added. The mixture is stirred for 30 minutes at room temperature. 1.42 Parts of methyl iodide is added portionwise at room temperature and the resultant mixture is stirred overnight in a nitrogen atmosphere. The mixture is then poured into water and extracted with methylene chloride. The methylene chloride extract is dried over anhydrous calcium sulfate and stripped under reduced pressure to give N-(2-diisopropylaminoethyl)-6,7-dimethoxy-N-methyl-1-phenyl-3,4-dihydro-2(1H)-isoquinolinecarboxamide.

What is claimed is:
1. A compound of the formula

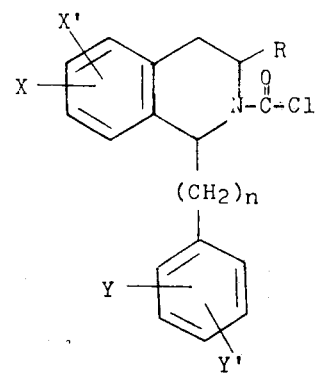

wherein X and X' are each selected from the group consisting of hydrogen, lower alkoxy, benzyloxy, and methyl, or X and X' together represent a single methylenedioxy or ethylenedioxy group; Y and Y' are each selected from the group consisting of hydrogen, halogen, lower alkoxy, and methyl; n is selected from the group consisting of 0 and 1; and R is selected from the group consisting of hydrogen and methyl.

2. A compound according to claim 1 which is 6,7-dimethoxy-3-methyl-1-phenyl-3,4-dihydro-2(1H)-isoquinolinecarbonyl chloride.

3. A compound according to claim 1 of the formula

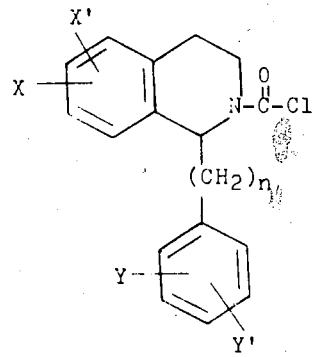

wherein X and X' are each selected from the group consisting of hydrogen, lower alkoxy, benzyloxy, and methyl, or X and X' together represent a single methylenedioxy or ethylenedioxy group; Y and Y' are each selected from the group consisting of hydrogen, halogen, lower alkoxy, and methyl; and *n* is selected from the group consisting of 0 and 1.

4. A compound according to claim 1 which is 1-benzyl-6,7-dimethoxy-3,4-dihydro-2(1H)-isoquinolinecarbonyl chloride.

5. A compound according to claim 1 of the formula

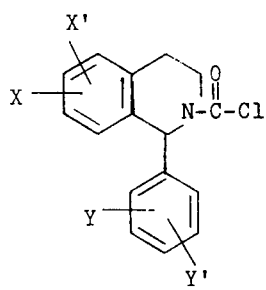

wherein X and X' are each selected from the group consisting of lower alkoxy, and benzyloxy, or X and X' together represent a single methylenedioxy or ethylenedioxy group; and Y and Y' are selected from the group consisting of hydrogen, halogen, lower alkoxy, and methyl.

6. A compound according to claim 1 which is 6-benzyloxy-7-methoxy-1-phenyl-3,4-dihydro-2(1H)-isoquinolinecarbonyl chloride.

7. A compound according to claim 1 of the formula

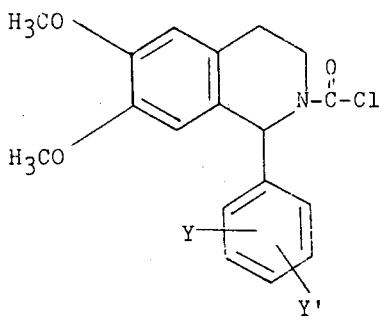

wherein Y and Y' are each selected from the group consisting of hydrogen, halogen, lower alkoxy, and methyl.

8. A compound according to claim 1 which is 6,7-dimethoxy-1-(4-methoxyphenyl)-3,4-dihydro-2(1H)-isoquinolinecarbonyl chloride.

9. A compound according to claim 1 which is 6,7-dimethoxy-1-(2-ethoxyphenyl)-3,4-dihydro-2(1H)-isoquinolinecarbonyl chloride.

10. A compound according to claim 1 which is 1-(2-bromophenyl)-6,7-dimethoxy-3,4-dihydro-2(1H)-isoquinolinecarbonyl chloride.

* * * * *